US006190863B1

United States Patent
Okada et al.

(10) Patent No.: US 6,190,863 B1
(45) Date of Patent: Feb. 20, 2001

(54) SUGAR CHAIN-RECOGNIZING ANTIBODIES AND REMEDIES FOR HIV INFECTIOUS DISEASES

(75) Inventors: Hidechika Okada; Noriko Okada, both of Nagoya (JP)

(73) Assignee: Otsuka Pharmaceutical Co., Ltd., Tokyo (JP)

( * ) Notice: Under 35 U.S.C. 154(b), the term of this patent shall be extended for 0 days.

(21) Appl. No.: 09/077,091

(22) PCT Filed: Dec. 17, 1996

(86) PCT No.: PCT/JP96/03673

§ 371 Date: May 19, 1998

§ 102(e) Date: May 19, 1998

(87) PCT Pub. No.: WO97/22361

PCT Pub. Date: Jun. 26, 1997

(30) Foreign Application Priority Data

Dec. 18, 1995 (JP) ................................................ 7-329010

(51) Int. Cl.[7] ............................ C12Q 1/70; G01N 33/53; C12N 15/00; C07K 16/00; A61K 39/395

(52) U.S. Cl. ........................... 435/5; 435/7.1; 435/343.2; 530/387.5; 530/388.35; 424/130.1

(58) Field of Search ........................... 530/387.5, 388.35; 435/5, 7.1, 363.2; 424/130.1

(56) References Cited

PUBLICATIONS

Wu, et al., IgM natural antibody against an asialo–oligosaccharide, gangliotetraose (Gg4), sensitizes HIV–1 infected cells for cytolysis by homologous complement, Intern. Immunol. vol. 8, No. 1, pp. 153–158, see Fig. 3A, 3B and 4; p. 153, column 2, firs, Jan. 1996.*

Fahey et al., Status of immune–based therapies in HIV infection and AIDS, Clin. exp. Immunol. 88, 1–5, see page 3, second column, third full paragraph, Jan. 1992.*

Fox, J. L., No winners against AIDS, Bio/Tech, vol. 12, p. 128, see entire page, Feb. 1994.*

Xiaoshan Wu et al., "Complement–Mediated Anti–HIV–1 Effect Induced by Human IgM Monoclonal Antibody Against Ganglioside GM[1] ", 1999, The American Association of Immunologists, pp. 533–539.

Watarai, Shinobu et al., "Application of Liposomes to Generation of Monoclonal Antibody to Glycosphingolipid: Production of Monoclonal Antibody to GgOse$_4$Cer", J. Biochem. 1987, vol. 102, No. 1, pp. 59–67.

Sanai, Yutaka et al., "Monoclonal antibody directed to a Hanganutziu–Deicher active ganglioside, $G_{M2}$(NeuGc)", Biochimica et Biophysica Acta, 1988, vol. 958, pp. 368–374.

Vrionis, Fotios D. et al., "Five New Epitope–defined Monoclonal Antibodies Reactive with $G_{M2}$ and Human Glioma and Medulloblastoma Cell Lines", Cancer Res., 1989, vol. 49, pp. 6645–6651.

Livingston, Philip O. et al., "Characterization of IgG and IgM Antibodies Induced in Melanoma Patients by Immunization with Purified $G_{M2}$ Ganglioside", Cancer Res., 1989, vol. 49, pp. 7045–7050.

(List continued on next page.)

Primary Examiner—Hankyel Park
(74) Attorney, Agent, or Firm—Sughrue, Mion, Zinn, Macpeak & Seas, PLLC

(57) ABSTRACT

The present invention is directed to a sugar-chain-recognizing antibody which belongs to the IgM isotype and which recognizes Gg4Cer(Galβ1-3GalNAcβ1-4Galβ1-4GlcβCer) or GM2 which appears on HIV infected cells, as well as to a therapeutics for HIV diseases containing those IgMs.

5 Claims, 5 Drawing Sheets

OTHER PUBLICATIONS

Hiraiwa, Nozomu et al., "Gangliosides and Sialoglycoproteins Carrying a Rare Blood Group Antigen Determinant, Cad, Associated with Human Cancers as Detected by Specific Monoclonal Antibodies", Cancer Res., 1990, vol. 50, pp. 5497–5503.

Ohta, So et al., "Cytotoxicity of Adriamycin–Containing Immunoliposomes Targeted with Anti–Ganglioside Monoclonal Antibodies", Anticancer Research, 1993, vol. 13, pp. 331–336.

Shitara, Kenya et al., "Immunoglobulin class switch of anti–ganglioside monoclonal antibody from IgM to IgG", Journal of Immunological Methods, 1994, vol. 169, pp. 83–92.

Guijo, Carmen Garcia et al., "Presence and isotype of anti–ganglioside antibodies in healthy persons, motor neuron disease, peripheral neuropathy, and other diseases of the nervous system", Journal of Neuroimmunology, vol. 56, 1995, pp. 27–33.

Livingston, Philip O. et al., "Vaccines containing purified GM2 ganglioside elicit GM2 antibodies in melanoma patients", Proc. Natl. Acad. Sci. USA, 1987, vol. 84, pp. 2911–2915.

DeGasperi, Rita et al., "Isolation and Characterization of Gangliosides with Hybrid Neolacto–Ganglio–type Sugar Chains", J. Biol. Chem., 1987, vol. 262, No. 35, pp. 17149–17155.

Ilyas, Amjad A. et al., "Gangliosides $G_{M2,}$ $IV^4GalNAcG_{M1b}$, and $IV^4GalNAcG_{Dla}$ as Antigens for Monoclonal Immunoglobulin M in Neuropathy Associated with Gammopathy", J. Biol. Chem., 1988, vol. 263, No. 9, pp. 4369–4373.

Nakao, Toru et al., "Novel Lacto–Ganglio Type Gangliosides with $G_{M2}$–epitope in Bovine Brain Which React with IgM from a Patient of the Amoytrophic Lateral Sclerosis––like Disorder", J. Biol. Chem., 1993, vol. 268, No. 28, pp. 21028–21034.

Nakamura, Kazuyasu et al., "Chimeric Anti–Ganglioside $G_{M2}$ Antibody with Antitumor Activity", Cancer Res., 1994, vol. 54, pp. 1511–1516.

Kitamura, Kunio et al., Serological response patterns of melanoma patients immunized with a GM2 ganglioside conjugate vaccine, Proc. Natl. Acad. Sci., USA, Mar. 1995, vol. 92, pp. 2805–2809.

Matsuda, Hazuhiro, Glycosphingolipid compositions of human T–lymphotropic virus type I (HTLV–I) and human immunodeficiency virus (HIV)–infected cell lines, Biochimica et Biophysica Acta, 1993, vol. 1168, pp. 123–129.

McAlarney, T. et al., "Specificity and Cross–Reactivity of Anti–Galactocerebroside Antibodies", Immunological Investigations, 1995, vol. 24, No. 4, pp. 595–606.

Long, Deborah et al., "Characterization of Human Immunodeficiency Virus Type 1 gp 1 20 Binding to Liposomes Containing Galactosylceramide", Journal of Virology, 1994, vol. 68, No. 9, pp. 5890–5898.

Cook, Davis G. et al., Binding of Human Immunodeficiency Virus Type 1 (HIV–1) Gp 1 20 to Galactosylceramide (GalCer): Relationship to the V3 Loop, Virology, 1994, vol. 210, pp. 206–214.

International Search Report.

Xiaoshan Wu et al., "Complement–Mediated Anti–HIV–1 Effect Induced by Human IgM Monoclonal Antibody Against Ganglioside GM", 1999, The American Association of Immunologists, pp. 533–539.

* cited by examiner

SUGAR CHAIN-RECOGNIZING ANTIBODIES AND REMEDIES FOR HIV INFECTIOUS DISEASES

TECHNICAL FIELD

The present invention relates to novel sugar-chain-recognizing antibodies, and more particularly to antibodies which belong to the class IgM and which recognize sugar chains expressed in HIV-infected cells, as well as to remedies for treating HIV-patients containing the antibodies as effective ingredients.

BACKGROUND ART

AIDS (acquired immunodeficiency syndrome) was first discovered in San Francisco in 1981 as a fatal immunodeficiency disease of homosexual males (Gottlieb, M. S., Schroff, R., et al., N. Engl. J. Med., 305, 1425–1430(1981)). Two years later, the Montanie group of the Pasteur Institute in France discovered the virus that causes AIDS (Barre-Sinoussi, F., Chermann, J. C., et al., Science, 220, 868–871 (1983)). In 1985, this virus was univocally named HIV (human immunodeficiency virus) (Coffin, J., Haase, A., et al., Science, 232, 697(1986)).

AIDS is a disease having the following features and effects: When an individual is infected with HIV through sexual intercourse, blood transfusion, etc., the virus destroys the immunological functions of the infected individual, causing acquired immunodeficiency of the host, i.e., the infected individual. Eventually, the host manifests a variety of symptoms such as diarrhea and pneumonia, resulting in a final outcome of death of the host.

Presently, many researchers are attempting to develop remedies for AIDS. For example, since the discovery of azidothymidine (AZT) by Mitsuya et al. (Mitsuya, H., et al., Proc. Natl. Acad. Sci., USA., 82, 7096(1985)), ddI (2', 3'dideoxyinosine), ddC (2',3'-dideoxycytidin), and other substances have been studied in clinical situations. However, pharmaceuticals providing satisfactory results have not yet been reached.

Although the incubation period from infection with HIV to onset of disease greatly varies depending on the individual, about 50% of humans who are infested with HIV manifest the disease with certainty within 10 years after infection, and almost all the infected patients die within 1 to 3 years after manifestation of the disease. Adults over 40 years of age and children rapidly develop the disease after they are infected with HIV. Reasons that explain the grace period between infection and development of AIDS-related complex (ARC) may include the patients' general health conditions, genetic predisposition, complications with other infection disease, and other host-dependent causes, as well as differences in the strain of infectious virus.

In cases of infection due to transfusion of blood components, most HIV-infected individuals manifest AIDS and die. However, some infected individuals do not manifest AIDS even after 10 years have passed after infection, and some other infected individuals take an even longer time before manifestation of AIDS. Such cases are seen worldwide, and it has been reported that 5% of HIV-infected individuals survive for long periods. So-called long-time survivors among HIV-infected persons, who stay asymptomatic for long periods, have received much attention, because they are considered to offer a clue for elucidation of the mechanism of their resistance to HIV virus or preventing the manifestation of the pathological symptoms. Therefore, a variety of studies and research have been performed on such long-time survivors.

However, the reason why longtime survivors do not manifest AIDS in spite of having been infected with HIV has not yet been clearly understood. Thus, it is desired to clarify the reason of HIV resistance, and to develop remedies for treating HIV diseases on the basis of the reason.

DISCLOSURE OF THE INVENTION

The present inventors studied the difference between the silent cases and active cases of virus replication among HIV-infected persons. During the studies, they found that specific IgMs found among natural antibodies for certain sugar chains carried by some infected patients might explain the delay of disease development. The sugar chains that serve as antigens are considered not to exist in the body under usual circumstances' or to exist in a limited amount. However, when cells are infected with HIV, the sugar chains appear on the surfaces of T cells or macrophages. (Generally speaking, it is well known that then cells becomes tumor or are infected with a virus, special sugar chains appear on the surfaces of the cells). If antibodies for such sugar chains belonging to the class IgM are present in serum as natural antibodies, the antibodies recognize HIV-infected cells and are bound to the infected alls. Complements cascade is activated at the local site, where IgM bound to the sugar antigen, and results in lysis of the HIV-infected cells. Thus, serum that contains the aforementioned natural IgM antibodies establishes a special environment in which HIV-infected cells do not easily proliferate. Also, the present inventors found that the HIV-infected cells have enhanced complement sensitivity. These facts have been confirmed not only in vitro but also in patients who had been infected with HIV whose manifestation of AIDS was delayed. Namely, it was actually confirmed that such long lived patients bare antibodies belonging to the class IgM that are reactive with HIV-infected cells.

It was also found that cells that are usually resistant against complements are lysed by the complements after antibodies for gangliotetraose (Gg4) are bound to such cells. In addition, antibodies Belonging to the class IgM having binding capacity to the infected cells eliminate infected cells as a result of cytolysis mediated by complements activation and make a hole to the HIV infected cells. Accordingly, it has been learned that administration of antibodies belonging to the class IgM a nd having reactivity with HIV-infected cells is useful for the treatment of HIV-carriers.

Accordingly, the present intention provides a sugar-chain-recognizing antibody which belongs to the class IgM and which recognizes Gg4Cer(Galβ1-3GalNAcβ1-4Galβ1-4GlcCer) or GM2.

The present invention also provides a remedy for HIV diseases (AIDS) containing the sugar-chain-recognizing antibody as an effective substances The present invention also provides a composition for treating HIV diseases with the sugar-chain-recognizing antibody.

The present invention also provides the use of the sugar-chain-recognizing antibody and the manufacturing method for a thrapeutics for HIV diseases.

The present invention also provides a method for treating HIV-infected patients, which is characterized by the administration of an effective amount of the sugar-chain-recognizing antibody to HIV patients.

BEST MODE FOR CARRYING OUT THE INVENTION

Figure 1:
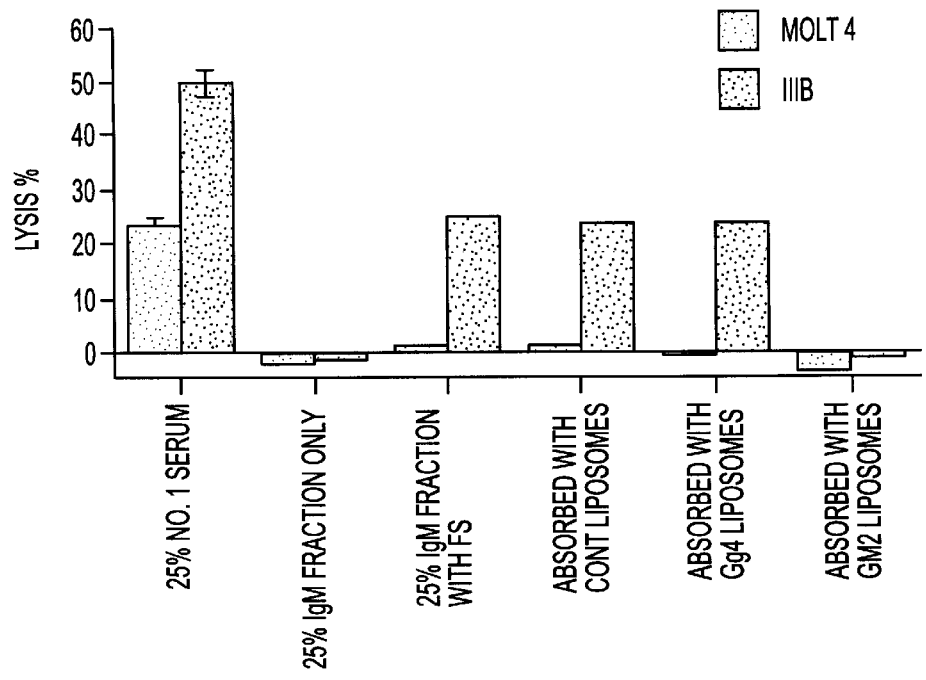
FIG. 1 is a graph showing the results of an epitope analysis performed on serum sample No. 1.

As used herein, sugar chains are represented by customary abbreviations in the art; Gg stands for ganglio, Cer for ceramid, Gal for galactose, GalNAc for N-acetylgalactose, and Glc for glucose. The antibodies of the present invention may be separated from human serum, or they may be prepared through a conventional method for raising antibodies using Gg4Cer or GM2 as the antigen, so long as the antibodies recognize Gg4Cer or GM2 (ganglioside GM2: II$^3$αNeuAc-GgOse$_3$Cer) and belong to the immunoglobulin class as IgM.

In order to separate the antibodies of the present invention from human serum, these may be used ordinary methods for screening the presence of antibodies employing Gg4Cer or GM2 as an antigen. The serum may be one collected from sero negative HIV-infected patient or others derive from healthy individual. The antibody against Gg4Cer or GM2 may be obtained through a conventional method such as a hybridoma method or a method using EB virus immortalization.

Techniques that may be use(for the screening include conventional ELISA, RIA, fluorescent antibody technique, dot-immunobinding assay, the Western blotting method, and the $^{51}$Cr-release method.

After being separated from the aforementioned sera, the antibodies of the present invention may be purified easily using well-known immunoglobulin purifying methods. Examples of such means include salt precipitation, gel filtration, and affinity chromatography (using i mannan column with which a mannose polymer is coupled for removing mannose binding protein (MBP).

The antibodies of the present invention may also be prepared through a conventional hybridoma method using Gg4Cer or GM2 as the antigen. The antibodies of the invention may be monoclonal or polyclonal, so long as they recognize Gg4Cer and/or GM2 and belong to IgM class.

The antibodies of the present invention are useful for the treatment of HIV diseases, as can be confirmed from the following.

The present inventors obtained a human serum sample that had a capacity of causing cytolysis of HIV-1 infected T cell lines. A human T cell line (MOLT4) infected with the HTLV-IIIB strain of HIV-1 was found to be lysed by fresh normal human serum (NHS) from a healthy individual who was HIV-seronegative, although most of serum examined, including HIV-infected carriers' sera, were not active to lysis the HIV infected Molt 4. When a fresh sample was again taken one year after the initial sample was obtained, the serum with ability to lyse HIV-infected ce ls was still potent to the same extent. The cytotoxic capacity of NHS-1 was abolished by heating the serum at 56° C. for 30 minutes, and was restored by the addition of a non-lytic fresh serum (NHS-5), indicating that the cytolysis had been mediated by complements activation, because heat treatment is known to inactivate complements.

Mannose-binding protein (MIP) in serum has been reported to react with gp41 (C. F. Ebenbichler et al., J. Exp. Med., 174, 1417 (1991)) and gp120 (C. Sual et al., J. Immunol. Med., 152, 6028 (1994)) of HIV, to thereby exhibit complement activities. However, when MBP was removed from NHS-1 using a mannan column, cytolytic capacity was not reduced.

After fractionation of NHS-1 by gel filtration on a TSK gel G3000 SW column, the IgM fraction was found to have the capacity to sensitize HIV-infected MOLT4 cells (HIV-MOLT4) for cytolysis by non-lytic human serum such as NHS-5. The fraction completely lost its sensitizing capacity abolished by being passed through an affinity column coupled with a mouse anti-human IgM monoclonal antibody. This explains that IgM is responsible for the sensitization of HIV-MOLT4 to cytolysis by serum complements. However, this IgM did not react with HIV antigens in Western blot analysis. Therefore, the present inventors speculated that the antigenic epitope(s) recognized by this antibody might be altered sugar moieties produced due to HIV-infection. The inventors then attempted to treat uninfected MOLT4 cells with neuraminidase, and found that the treated cells were reactive with the IgM, which recognize a sialoglyco conjugate. Furthermore, absorption of the IgM fraction with these neuraminidase-treated MOLT4 cells significantly reduced sensitization to cytolysis by normal human serum.

The IgM fraction showed reactivity with certain glycosides, such as Gg4Cer(Galβ1-3GalNAcβ1-4Galβ1-4GlcβCer), which can be generated by removed of sialic acid from GM1. Furthermore, liposomes bearing Cg4 absorbed the sensitization capacity of the IcM for cytolysis. The presence of Gg4 antigen-recognition sites on HIV-MOLT4 cells and on neuraminidase-treated MOLT4 cells was confirmed by immunostaining with mouse anti-Cg4 monoclonal antibody. These actions were also confirmed with IgM that recognized GM2 antigen or HIV-infected V-937 cells.

On the other hand, complement activities are known to be suppressed by specific membrane inhibitors such as (1) a decay accelerating factor which is a inhibitor for membrane complements (DAF; A. Nicholson-Weller, J. Burge, D. T. Fearon, P. F. Weller, K. F. Austen, J. Immunol., 129, 184 (1982)), (2) membrane cofactor proteins (MCP; T. Seya, J. R. Turner, J. P. Atkinson, J. Exp. Mel., 163, 837 (1986)), and (3) CD59 (HRF20; 20 kDa homologous restriction factor, N. Okada, R. Harada, T. Fujita, H. Okada, Int. Immunol., 1, 205 (1989); A. Davis et al., J. Exp. Med., 170, 637 (1989)).

Under conditions in which Fas antigen was expressed, expressions of DAF, MCP, and CD59 were down-regulated, whereas expression of HLA-DR retained unchanged. In particular, expression of CD59 on HIV-infected cells was not greater than 50% that of uninfected MOLT4 cells. Down regulation of CD59 expression was also evident from the level of mRNA as determined by Northern blot analysis.

Moreover, HIV-infected-MOLT4, whose resistivity against complement reaction is weakened due to reduced expression of CD59, is subject to selective cytolysis by IgM and normal human serum complements. There was no difference in the extent of gp120 expression between lysed and unlysed cells. The down regulation of DAF, MCP and particularly of CD59, might contribute to cytolysis of the HIV-infected cells by human complements activated by antigen-IgM complex. Furthermore, a reduction in the amounts of terminal sialic acid on the membranes of HIV-infected cells might facilitate the activation of complements. However, HIV-infected cells are not lysed by HIV-seronegative serum complements even though the cells bound IgG that can be detected by fluorescein-labeled anti-human IgG antibodies.

For complement activation by IgG via the classical pathway, two IgG molecules reacting in close proximity to each other, are required. On the other hand, only one molecule of IgM is sufficient for complement activation. Therefore, complement activation can be triggered much more efficiently by IgM than by IgG.

Furthermore, it is possible that complement activation initiated by IgM may escape from restriction by complement-inhibiting molecules on the target cell membranes, since IgM is a large molecule having a molecular size of 900 kDa and complement components bound to the molecule might not be accessible to DAF, MCP, or other complement-inhibiting molecules on the membranes. On the other hand, membrane attack complexes generated by the activation of complements bind to the lipid bilayer of cell membranes. CD59 restricts the formation of these antigen-2gM complexes that are bound to the membranes, and thereby prevent cell damage. Reduced expression of CD59 on HIV-infected cells revert the resistance of cells against membrane attack complexes and accelerates cytolysis.

The same results as with MOLT4 cells were obtained with other T cell lines such as CEM and MT4 cells. HIV-infected CEM cells showed reduced CD59 expression and were sensitive to cytolysis by the IgM and complements. However, no reduction in CD59 expression was observed in macrophage cell lines such as HIV-infected U937 cells, and these cell lines were resistant to cytolysis mediated by the IgM and complements.

Cytolytic reactions mediated by IgM and complements may play a role in vivo in the elimination of HIV-infected T cells. If an individual has natural IgM antibodies reactive with sugar antigens, such as Gg4 and GM2, that appear on HIV-infected T cells, it is considered that expansion of HIV infection may be suppressed upon HIV infection. Although HIV-infected macrophages may survive the attacking reaction involving IgM and complements and may remain as a reservoir of HIV, infected T lymphocytes will be removed. Thus, serum of IgM would be a key factor in a mechanism responsible for the long-term survival of some HIV-carriers. In fact, when twenty long-term survivors who lad survived 12 years or more after infection with HIV were studied, all of them were found to possess IgM, whereas five individuals who manifested symptoms within short periods possessed only IgG and did not possess IgM.

A similar protective mechanism of IgM has also been found with melanoma patients (Ores, P. C., Sze, L. L., Morton, D. L. and Irie, R. F., J. Natl. Cancer Inst., 66, 249, 1980).

As described above, administration of the sugar-chain IgM of the present invention to HIV-infected patients would be effective in retaining natural antibodies in the body, and thus would be effective in the treatment and prevention of AIDS.

The IgM of the present invention is generally incorporated into suitable drug preparations typified by parenteral preparations such as injections, and is administered to patients in need of treatment. Such preparations may be obtained through customary methods, and vehicles for the preparations may be conventional and general ones such as sugar, amino acids, and proteins. The preparations contain— in addition to the IgM of the present invention—suitable additives such as a variety of inorganic salts in suitable amounts. The dose of the preparations of the present invention in various forms is not particularly limited. It is generally preferred that the dose be determined to exhibit activity such that the IgM is present in an amount ranging from 10 $\mu$g/ml to 50 $\mu$g/ml in vitro with respect to the effective ingredient sugar chains (IgM potency) and kills HIV-infected cells.

Thus, the antibodies of the present invention are useful for the prevention and treatment of HIV-infected patients. That is, when the sugar-chain specific antibodies of the present invention are administered to an individual, natural antibodies titer are raised in vivo, to thereby provide therapeutic and preventive effects against AIDS.

EXAMPLES

The present invention will next be described in more detail by examples.

Example 1

Culturing of Cells

MOLT4 cells, a human T cell line, were grown in RPMI 1640 medium supplemented with 10% fetal calf serum (FCS), 2 mM glutamine, 100 IU/ml penicillin and 100 mg/ml streptomycin, and were kept free from mycoplasma. The cells were infected with HLTV-IIIB (HIV-1) and cultured for 4 weeks or more before being used as a source of HIV-infected terget cells. More than 95% of the cells were HIV-env antigen (gp120) positive as detected by flow cytometry using a monoclonal antibody 0.5$\beta$ (i.e., an antibody for gp120 of HTLV-IIIB), thereby confirming that infection with HIV-1 prevailed among most of the cells.

$5 \times 10^6$ HIV-infected MOLT4 cells and uninfected control MOLT4 cells (normal MOLT4) were separately labeled with $^{51}$Cr. After labeling, cells were both washed and resuspended in serum free RPMI 1640 medium at a concentration of $2 \times 10^5$/ml.

A 100 $\mu$l aliquot of the cell suspension and 100 $\mu$l of each of fresh or heat-inactivated sera were placed in each well of U-bottom microplates. The sera were obtained from four HIV-seropositive patients and thirteen healthy HIV-seronegative donors.

The plates were incubated at 37° C. for 1.5 hours and centrifuged. The percentage of $^{51}$Cr release into the cell-free supernatant was computed by the following equation:

$$\% \, ^{51}\text{Cr release} =$$
$$\{(\text{release with fresh serum} - \text{release with heat-inactivated serum})/$$
$$(\text{release with 5\% Triton} \times 100 -$$

-continued release with heat-inactivated serum)} × 100

Example 2

Treatment with Neuraminidase

One hundred (100) µl of neuraminidase were added to 100 µl of cell suspension (2×10⁶) and incubated at 37° C. for 45 minutes. To cell pellets of 2×10⁶ MOLT4, Neu-MOLT4, or HIV-MOLT4, 250 µl of an IgM fraction (250 µg/ml) from NHS1—the serum that exhibited strong cytolysis activity were added and incubated at 4° C. for 30 minutes. After centrifugation, the supernatants were transferred to other tubes for determination of their sensitizing capacity. The cells were washed and stained with FITC-conjugated mouse anti-human IgM and analyzed on a FACScan.

The supernatants obtained after incubation with MOLT4, Neu-MOLT4, or HIV-MOLT4 were incubated with HIV-MOLT4 in the presence of non-lytic human serum (NHS-5) to determine the cytolysis activity.

Example 3

Ninety-five serum samples from healthy individuals were subjected for screening as described in Example 1 in which infected MOLT4 cells labeled with $^{51}$Cr were used as target. As a result, 16 individuals were found to exhibit 15% or higher cytolysis activity for infected cells. Subsequently, through use of infected U937 and MOLT4 cells, selection was made to two serum samples that Exhibited cytolysis activity to these two infected cell lines. The IgM fractions of the sera were collected and used in the following experiment.

Liposomes were prepared in accordance with the method described in Immunology, 48: 129–140 (1983). Briefly, cholesterol, dimyristoyl-phosphatidylcholine, and one of a variety of lipids to be inserter were mixed at 1:1:0.1, and the solvent chloroform was evaporated with a rotary evaporator, to thereby create a lipid film on the interior surface of the flask. Control liposomes were prepared from cholesterol and dimyristoyl phosphatidylcholine (1:1) PBS was added to the lipid film, and the film was vigorously vibrated in a vortex mixer so as to form liposomes (multi-layered). PBS was added to the multi-layered liposomes for centrifugal washing, to thereby form a liposome suspension.

From the resultant liposome suspension, an aliquot containing 10 nmol glycolipids taken and subjected to centrifugation to thereby obtain a liposome pellet. The supernatant was discarded. To the pellet was added the IgM fraction (200 µg/200 µl) (after fractionation of seropositive serum through gel Filtration using TSK-3000). The mixture was stirred and allowed to stand at room temperature for 60 minutes so as to absorb antibodies for glycolipids present on the liposome membranes. After reaction, the mixture was centrifugated to precipitate the liposomes, and the supernatant was recovered.

The IgM fraction after the above absorption procedure was examined for the cell damaging activity to HIV-infected MOLT4 cells (HIV-MOLT4). Briefly, to 100 µl of $^{51}$Cr-labeled HIV-MOLT4 (i.e., $^{51}$-HIV-MOLT4, 2×10⁵/ml), or in the case of control, to the same amounts of uninfected $^{51}$-MOLT4, were added 50 µl of ar IgM fraction which had or had not undergone the absorption procedure and 50 µl of seronegative normal human serum (as a source of complements). The mixture was allowed to react at 37° C. for 90 minutes, and then the plates were centrifugated. The amount of $^{51}$Cr released into the supernatant was measured to obtain the level of damage to the cells.

Figure 2:
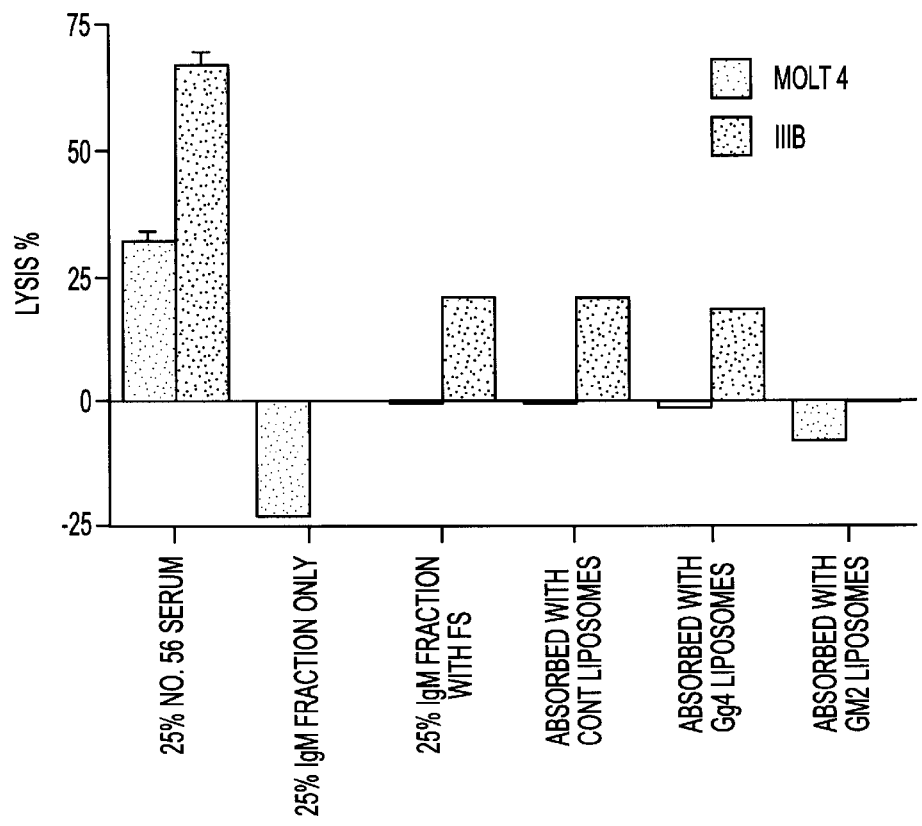
FIG. 2 is a graph showing the results of an epitope analysis performed on serum sample No. 56.

That is, the control liposomes, Gg4 liposomes, and GM2 liposomes, which were liposomes only, liposomes plus Gg2, and liposomes plus GM2, respectively, were used in the test. An antigen-antibody reaction was caused through use of one type of the liposomes, fresh serum, and a 25% IgM fraction. The cell lysing activity (% cytolysis) was determined in the supernatant. The results are shown in FIGS. 1 and 2. In both cases of sample No. 1 and No. 2, the lysing activity remained in "control" and "Gg4 iposomes," and this activity was completely eliminated upon contact with GM2 liposomes. From these results, it was confirmed that, in sera from healthy individuals, GM2 was the antigen epitope for IgM natural antibodies produced against HIV-infected cells.

Experiment Example 1

Figure 3A:
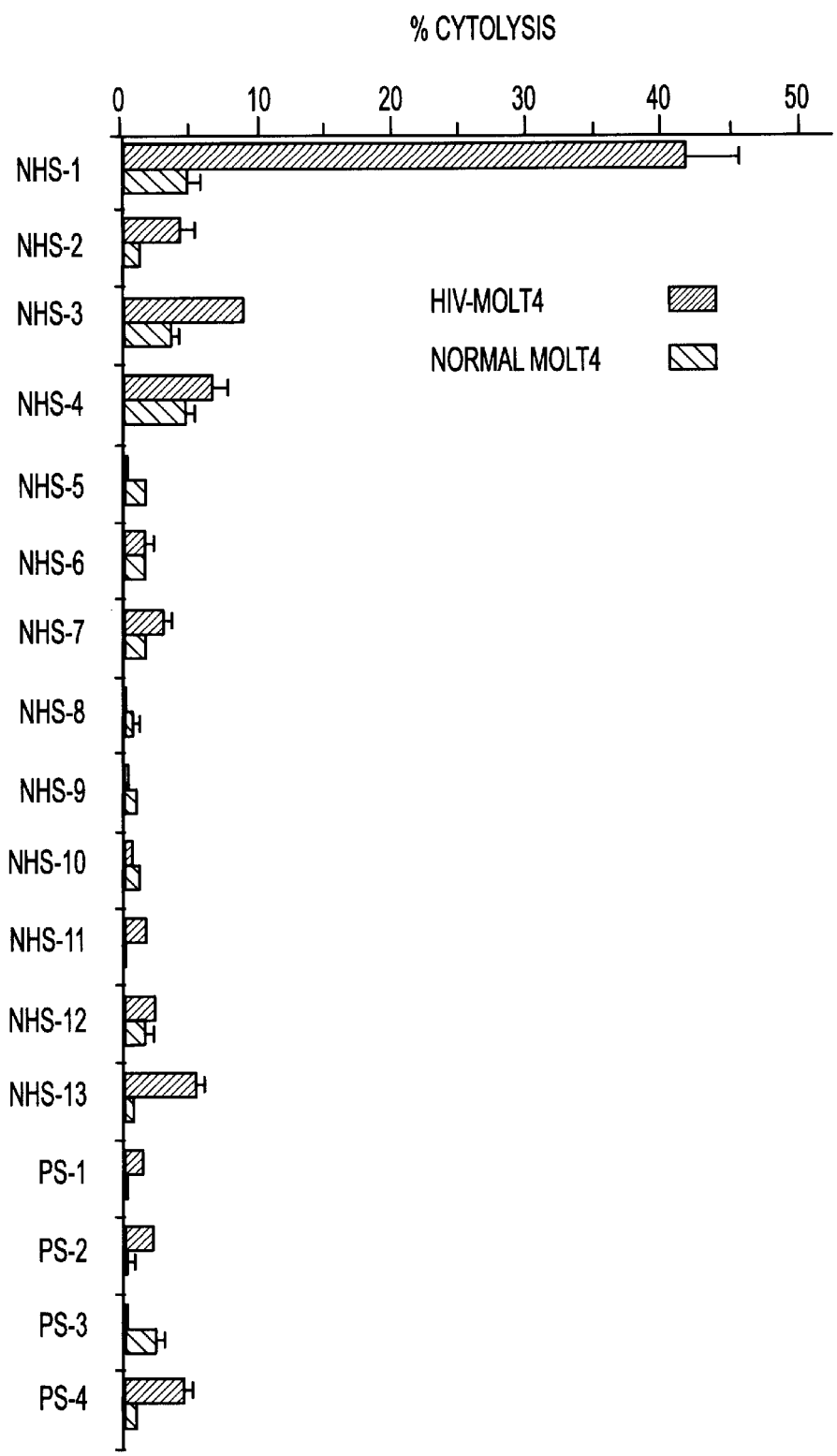
FIG. 3 is a graph showing the cytolysis capacity of HIV-infected-MOLT4 cells by human serum containing the IgM from individual who is a healthy HIV seronegative donor.
Figure 3B:
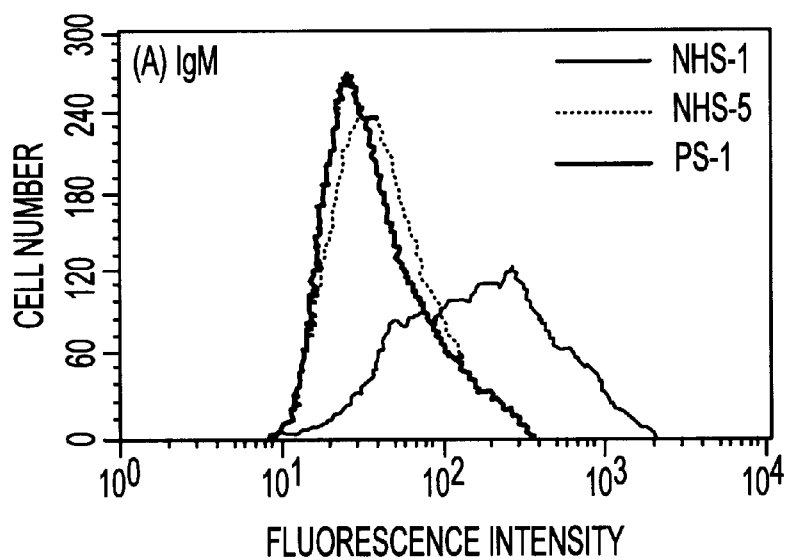
Figure 3C:
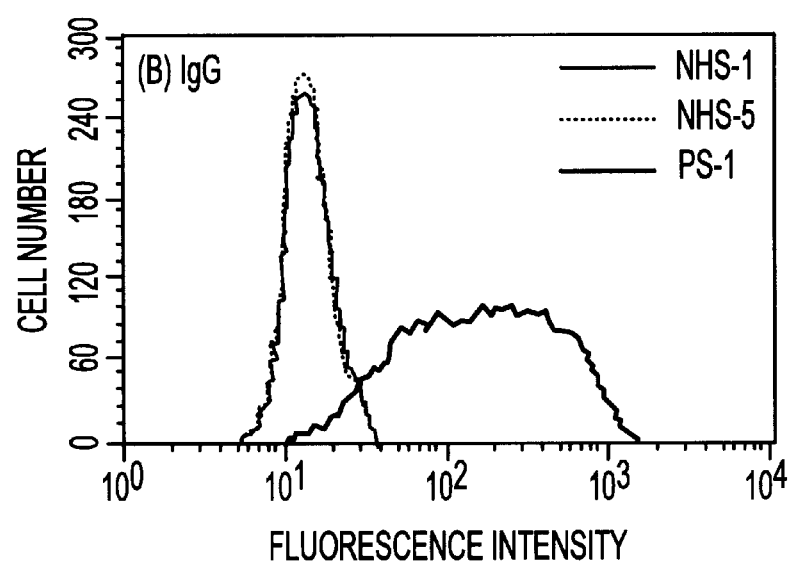

Cytolysis of HIV-MOLT4 Cells by Human Serum (containing IgM) from an Individual Who is a Healthy Seronegative Donor The results are shown in FIG. 3. The x-axis represents % cytolysis, and the y-axis represents sera from donors (NHS-1 through NHS-13 and PS-1 through PS-4). FIG. 3 is accompanied by charts (a) and (b) which show the results of immunostaining performed after reaction of a serum sample (NHS-1, NHS-5, or PS-1) with HIV-MOLT4 cells (x-axis: fluorescence intensity; y-axis: cell number), wherein chart (a) is drawn to the case in which IgM was used, and chart (b) is drawn to the case in which IgG was used. From these charts, the following observation become evident.

(A) Of the thirteen (13) sera from healthy HIV-seronegative donors, only one (NHS-1) caused cytolysis of $^{51}$Cr-labeled HIV-MOLT4 cells attributed to the human serum.

NHS-1 showed as high as 43% cytolysis, whereas no other serum from healthy individuals (twelve individuals from NHS-2 to NHS-13) showed any noticeable cytolysis. The sera from HIV-seropositive patients (PS-1 to PS-4) showed almost no cytolysis.

(B) HIV-MOLT4 cells were incubated with an equal volume of a serum sample, NHS-1 NHS-5, or PS-1, at room temperature for 30 minutes. The cells were then washed and immunostained by the use of FITC-labeled anti-human IgM antibody or FITC-labeled anti-human IgG antibody.

The results are shown in carts (a) and (b) of FIG. 3. The HIV-MOLT4 cells treated with NHS-1 was bound to the anti-IgM antibody, whereas PS-1 which was bound to the anti-IgG antibody, did not react with the anti-IgM antibody.

Experiment Example 2

Figure 4A:
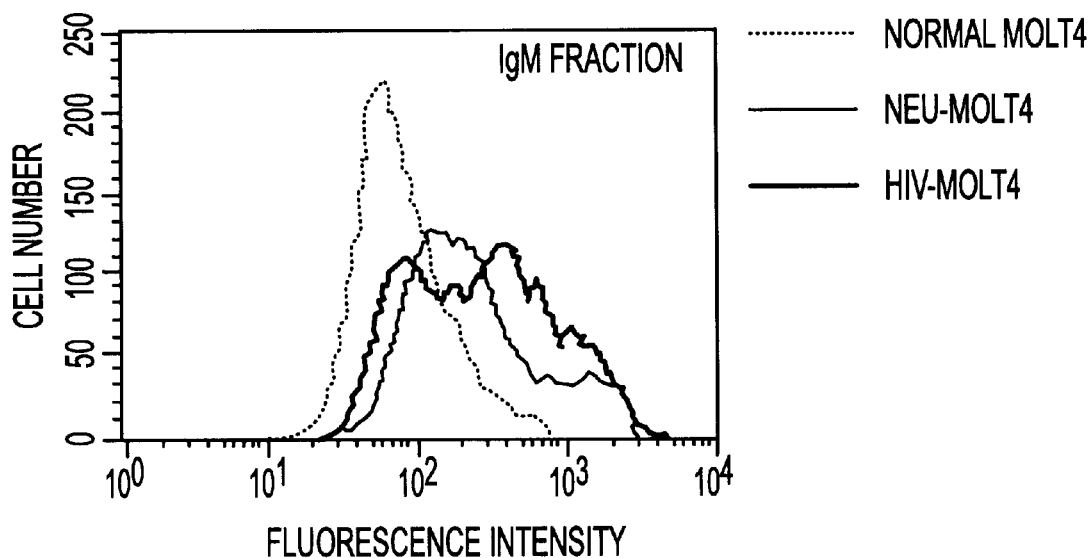
FIG. 4 is a graph showing the results of a test in which neuraminidase-treated MOLT4 cells, untreated MOLT4 cells, and HIV-MOLT4 cells were independently treated with an IgM antibody fraction from Normal human Serum-1 (NHS-1) (a), or with an anti-gp120 monoclonal antibody and then immunostained with fluorescein-labeled anti-human IgM antibody.
Figure 4B:
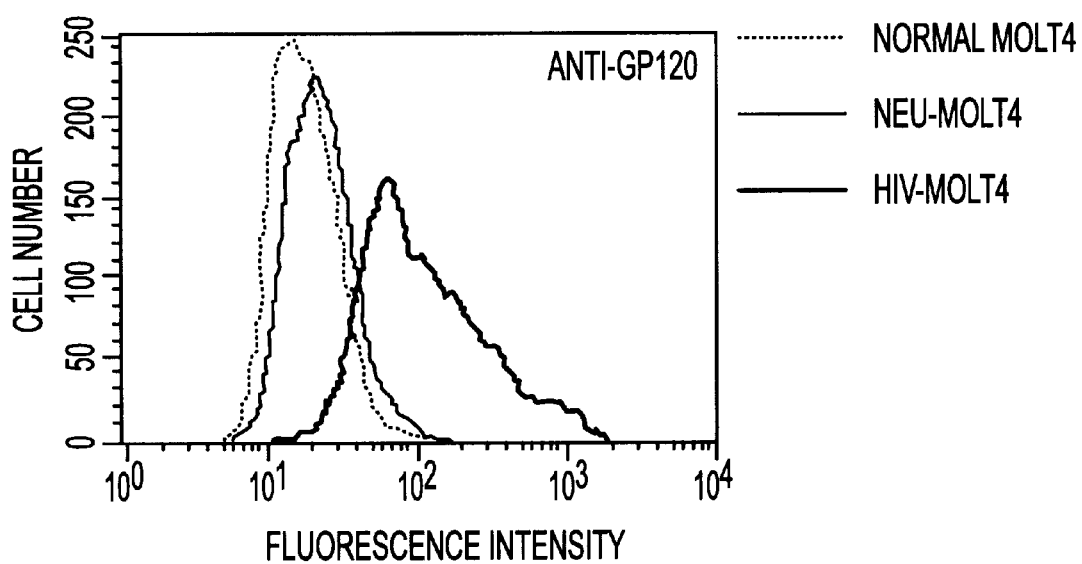

Neuraminidase-treated MOLT4 cells, untreated MOLT4 cells, or HIV-MOLT4 cells were treated with an IgM antibody fraction from NHS-1, and then immunostained with fluorescein-labeled anti-human IgM antibody. The results are shown in FIG. 4 similar to chart (a) of FIG. 3. The IgM antibody that reacted with HIV-MOLT4 cells also reacted with neuraminidase-treated HIV-MOLT4 cells.

As a result, as shown in chart (a) of FIG. 4, the IgM fraction from NHS-1 reacted with Neu-MOLT4 cells as strong as its reaction to HIV-MOLT4 cells. The anti-gp120 monoclonal antibody (anti-gp120, 0.5β) stained only HIV-MOLT4 cells as shown in chart (b) of FIG. 4.

The sensitizing capacity of the IgM fraction for cytolysis by human serum was absorbed by treatment with Neu- MOLT4 cells as was absorbed by treatment with HIV-MOLT4 cells. In other words, the IgM fractions treated with these cells for absorbing their cytolysis capacity lost the potency for imparting the healthy human serum (NHS-5) with cytolysing power.

Experiment Example 3

IgM that is reactive to HIV-MOLT4 reacts with Gg4Cer.

(A) Seven different types of glycolipids described below were chromatographed on a plastic TLC plate, to thereby detect spots through immunostaining by the use of orcinol-$H_2SO_4$ reagent and the IgM fraction obtained from NHS-1 (a), and also through TLC immunostaining by the use of the IgM fraction obtained from NHS-1.

1. LacCer, 2. Gg3Cer, 3. nLc4Cer, 4. Lc4Cer, 5. Gb4Cer, 6. Gg4Cer, 7. $IV^3Gal\alpha$-nLc4Cer.

Gg4Cer was significantly stained. LacCer, Gg3Cer, and LcCer were slightly stained. However, the IgM fraction barely reacted with nLc4Cer, Gb4Cer, $IV^3Gal\alpha$-nLc4Cer, sialylated glycolipids such as GM3, GM2, GM1, GD1a, GT1b, GQ1b, $IV^3NeuAc\alpha$-nLc4Cer, sialyl $Le^a$ and sialyl $Le^x$.

Levels of staining relative to Gg4Cer, level of which was taken as 100, were 25.8, 31.3, 0, 29.3, 0, and 24.6 for LacCer, Gg3Cer, nLcCer, Lc4Cer, Gb4Cer, and $IV^3Gal\alpha$-nLc4Cer, respectively.

Liposomes were prepared as described by Okada and others (Okada, N., Yoshida, T., and Okada, H., Nature, 299, 261 (1982)). An IgM fraction (50 μg/200 μl) was mixed with 5 nmol of each liposome preparation. After centrifugation, the cytolysis activity of supernatants was determined in accordance with the method described in Example 2.

Figure 5A:
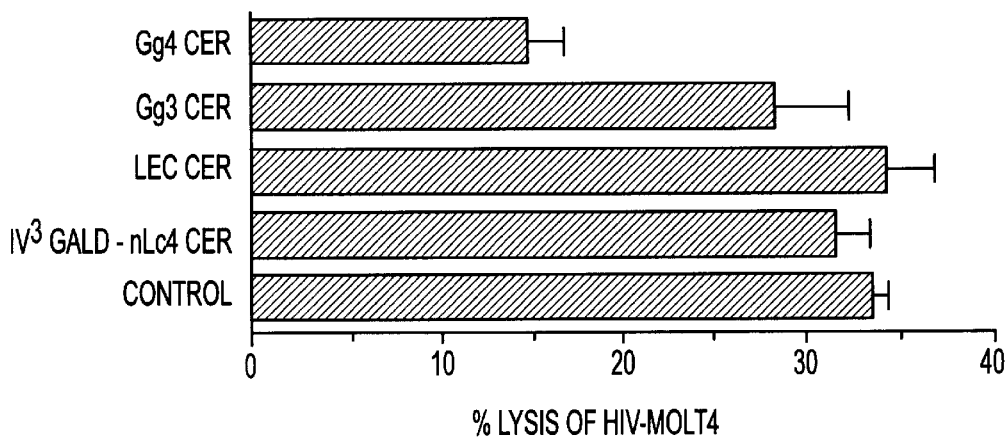
FIG. 5 is a graph showing -he results of the remaining cytolysis capacity of the IgM entibody, which is absorbed by various sugar coated liposomes is well as the results of immunostaining of the target cells treated by the IgM.
Figure 5B:
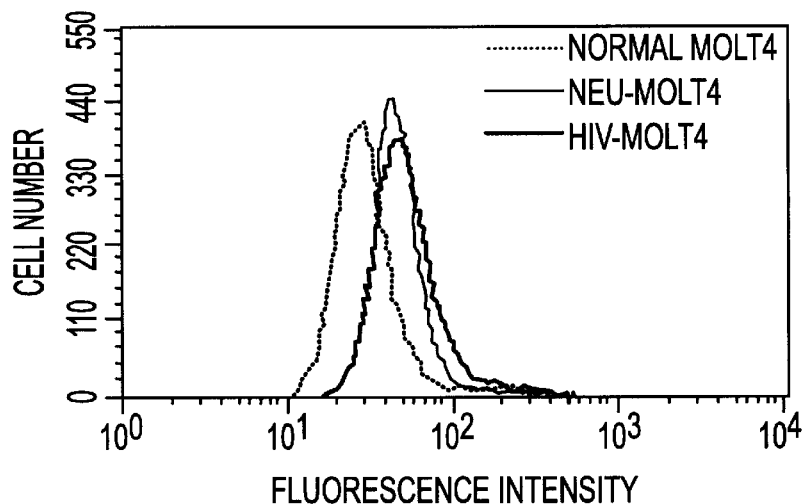

The capacity of the IgM fraction for cytolysis of HIV-MOLT4 cells by non-lytic human serum (NHS-5) was absorbed by treatment with Gg4-liposomes to a level lower than half (FIG. 5, A).

Although mouse monoclonal antibody against Gg4 did not react with normal MOLT4 cells, Lt reacted more with HIV-MOLT4 and Neu-MOLT4 cells as determined by flow cytometry analysis (FIG. 5, B).

Experiment Example 4

Figure 6:
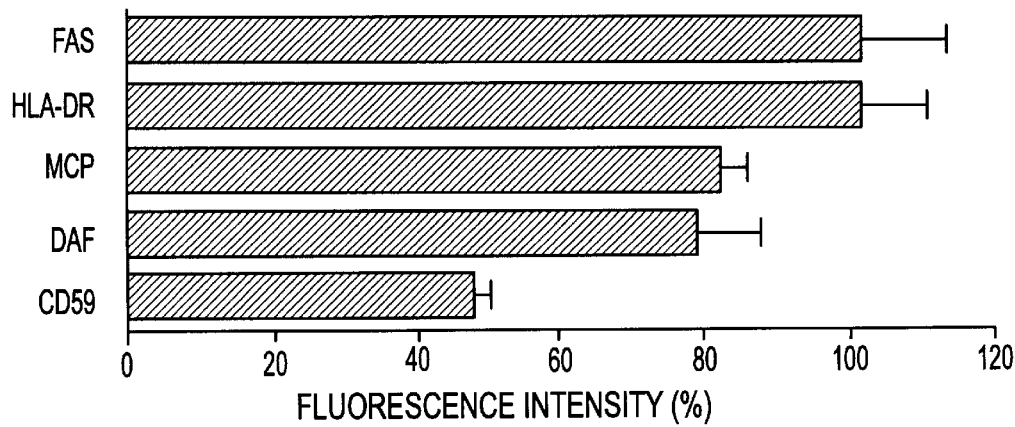
FIG. 6 is a graph showing -he results of flow cytometry for determining the amount of expression of complement inactivating membrane proteins on HIV-infected-MOLT4 cells.

Significant Decrease in CD59 on HIV-MOLT4 Cells (A) Through flow cytometry analysis, expression of complement regulatory membrane actors (DAF, MCP, and CD59) on HIV-infected cells was found to be reduced. Expressions of Fas antigen and HLA-DR remailed unchanged after HIV-infection (FIG. 6).

(B) For Northern blot analysis of complement regulatory membrane factors, 5 μg of total RNA from uninfected (N) and HIV-infected (H) MOLT4 cells were extracted and denatured with glyoxal and DMSO as described in Thomas, P. S., Method Enzymol., 100, 255-2 (1983). cDNA fragments of CD59, DAF, MCP, and GAPDH (glyceraldehyde-3-phosphate-dehydrogenase) were used as probes. Reduction of CD59 mRNA was clearly observed.

After $1 \times 10^6$ cells were incubated with NHS-1 for 30 minutes at 37° C., two color analysis was performed on HIV-MOLT4. Dead cells were detected by staining with propiodium iodide (PI). This allows discrimination of dead cells which are stained with PI and living cells which are not stained with PI. C5b-9 (MAC), CD59, and gp120 were stained with FITC-labeled monoclonal antibodies to these antigens. The results are summarized as follows.

(a) PI-stained cells (dead cells) after incubation with NHS-1 were stained a little more strongly than PI-staining negative cells, the latter cells indicating that these cells treated with larger amounts of C5b-9 and were not killed.

(b) NHS-1 does not induce PI positive dead cell in the presence of 10 mM EDTA.

(c) Cells expressing lower amounts of CD59 were stained with PI after the treatment with NHS-1, indicating that cells expressing lower level of CD59 were preferentially killed.

(d) Expression of gp120 was essentially the same between PI-stained cells (dead cells) and unstained cells (living cells), indicating that the amount of anti-gp120 antiboday and cell-killing capacity of NHS-1 are not directly related.

INDUSTRIAL UTILITY

Since administration of the sugar-chain-recognizing antibody to HIV-infected indivisuals cause cytolysis of HIV-infected cells through mediation of activation of complement, the sugar-chain-recognizing antibody of the present invention is useful in the treatment and prevention of AIDS.

What is claimed is:

1. A composition for treating HIV-infected T cells, said composition comprising a sugar-chain-recognizing antibody of the IgM subclass of immunoglobulins which recognizes Gg4Cer(Galβ1-3GalNAcβ1-4Galβ1-4GlcβCer) or GM2.

2. A pharmaceutical composition for treating HIV-infected T cells, said composition comprising a sugar-chain-recognizing antibody of the IgM subclass of immunoglobulins which recognizes Gg4Cer(Galβ1-3GalNAcβ1-4Galβ1-4GlcβCer) or GM2, and a pharmaceutically acceptable carrier.

3. A method for treating an HIV-infected patient comprising administering to said patient, an effective amount of a sugar-chain-recognizing antibody of the IgM subclass of immunoglobulins which recognizes Gg4Cer(Galβ1-3GalNAcβ1-4Galβ1-4GlcβCer) or GM2.

4. The method according to claim 3, wherein said HIV-infected patient in need of reducing HIV-infected T cells, is administered said Gg4Cer(Galβ1-3GalNAcβ1-4Galβ1-4GlcβCer) or GM2-recognizing IgM antibody.

5. The method according to claim 3, wherein said Gg4Cer (Galβ1-3GalNAcβ1-4Galβ1-4GlcβCer) or GM2-recognizing IgM antibody binds to an HIV-infected T cell, and through interaction of said antibody with serum complement, causes complement-mediated cytolysis of said HIV-infected T cell.

* * * * *